US006093558A

United States Patent [19]

Seed et al.

[11] Patent Number: 6,093,558

[45] Date of Patent: Jul. 25, 2000

[54] BINDING PROTEIN OF BIOLOGICALLY ACTIVE COMPOSITIONS TO AN ADHESIVE FORMULATION ON A SUBSTRATE

[75] Inventors: John Seed, Ellicott City, Md.; Brian Seed, Boston, Mass.

[73] Assignee: Edge Biosystems, Inc., Gaitherburg, Md.

[21] Appl. No.: 07/732,487

[22] Filed: Jul. 25, 1991

[51] Int. Cl.[7] .......................... C12N 11/14; C12N 11/08; C07K 17/02; C07K 17/08

[52] U.S. Cl. .......................... 435/176; 435/177; 435/179; 435/180; 435/181; 435/395; 435/396; 435/399; 435/401; 435/402; 530/811; 530/812; 530/814; 530/815; 530/816

[58] Field of Search .................................... 435/174, 176, 435/177, 180, 179, 181, 395, 396, 399, 401, 402; 436/531; 530/815, 811, 812, 814, 816

[56] References Cited

U.S. PATENT DOCUMENTS

| | | | |
|---|---|---|---|
| 3,705,084 | 12/1972 | Reynolds | 435/182 X |
| 3,796,634 | 3/1974 | Haynes et al. | 530/815 X |
| 4,016,293 | 4/1977 | Coughlin et al. | 435/99 X |
| 4,067,959 | 1/1978 | Bolz | 435/7.92 |
| 4,137,137 | 1/1979 | Machi et al. | 204/159.16 |
| 4,352,884 | 10/1982 | Nakashima et al. | 435/180 |
| 4,414,976 | 11/1983 | Schwarz et al. | 128/334 |
| 4,683,058 | 7/1987 | Lyman et al. | 210/359 |
| 4,714,786 | 12/1987 | Wuesi et al. | 568/633 |
| 4,752,638 | 6/1988 | Nowinski et al. | 525/54.1 |
| 4,882,226 | 11/1989 | Schutyser etal. | 435/180 X |
| 4,889,632 | 12/1989 | Svec et al. | 210/500.28 |
| 4,918,016 | 4/1990 | Leaba et al. | 435/176 |
| 4,923,610 | 5/1990 | Svec et al. | 210/637 |
| 4,923,978 | 5/1990 | McCormick | 536/27 |
| 4,973,466 | 11/1990 | Reich | 424/426 |
| 4,997,682 | 3/1991 | Coco | 427/362 |
| 5,010,009 | 4/1991 | Steele et al. | 435/249 |
| 5,015,677 | 5/1991 | Benedict et al. | 524/17 |
| 5,024,933 | 6/1991 | Yang et al. | 435/6 |
| 5,122,452 | 6/1992 | Yamazaki et al. | 435/180 X |

FOREIGN PATENT DOCUMENTS 0 244 688 11/1987 European Pat. Off. .

OTHER PUBLICATIONS

Lentz et al., J. Biomed. Mater. Res., 19(9), Nov.–Dec., 1985 pp. 1101–1115.

Schramm, et. al., Clin. Chem. 33,8, 1338–1342(1987).

Su, et al., *Analytical Biochemistry,* 174:650–657, 1988.

Loomis, Methods in Enzymology, vol. XXXI, pp. 528–544, 1974.

Ragan, et al., *J. Exp. Mar.Biol. Ecol.,* 30:209–221, 1997.

Ohi, et al., *J. Appl. Biochem.,* 2:398–413, 1980.

Buffone, et al., *Clin. Chem.,* 31:164–165, 1985.

*Primary Examiner*—David M. Naff
*Attorney, Agent, or Firm*—Banner & Witcoff, Ltd.

[57] ABSTRACT

Compositions and methods are provided for adhering and binding biologically active proteins and protein-containing composites to substrates. Adhesive formulations comprising a nonproteinaceous polymer of monomeric units comprising an aromatic moiety substituted with at least one hydroxyl group such as poly(p-hydroxy-styrene) are applied to substrates and subsequently contacted with proteins. Beads comprising a nonproteinaceous polymer of monomeric units comprising an aromatic moiety substituted with at least one hydroxyl group are also provided, and the beads are coated with a protein. Substrates to which the adhesive formulations have been applied, as well as the beads, can be used to adhere cells and tissues, to sort cell types, to perform immunoassays, to perform chromatography and to remove protein from samples.

27 Claims, No Drawings

BINDING PROTEIN OF BIOLOGICALLY ACTIVE COMPOSITIONS TO AN ADHESIVE FORMULATION ON A SUBSTRATE

TECHNICAL FIELD OF THE INVENTION

This invention relates to the area of adhesives and binding agents for proteins. More specifically it relates to the use of a polymeric substance which has high affinity for proteins, either in the form of an adhesive formulation or in the form of beads.

BACKGROUND OF THE INVENTION

Proteinaceous Polymeric Adhesives and Binding Agents

A variety of different polymeric formulations are known in the art for adhering to biological specimens which contain proteins. Often these are taught to have medical applications, such as in wound healing, implanting cells, organs, prostheses, dental implants, etc.

Erhan, U.S. Pat. No. 4,822,867 teaches the use of graft copolymers of synthetic moieties onto a protein backbone as useful for artificial skin and wound covering. Schwarz, U.S. Pat. No. 4,414,976 discloses the use of a formulation for tissue adhesion which comprises fibrinogen, factor XIII, albumin and a plasmin or plasminogen-activator inhibitor. Reich, U.S. Pat. No. 4,973,466 teaches a wound healing dressing which comprises flocculated fibronectin. Yang, U.S. Pat. No. 5,024,933 teaches the use of a protein preparation from mussels as an adhesive for tissues and cells on which nucleic acid hybridization can be performed. Benedict, U.S. Pat. No. 5,015,677 discloses a composition containing a decapeptide component of a mussel polyphenolic protein in addition to a cross-linking agent. The composition can be used for repairing bones, in ophthalmic surgery, for dental devices, for grafting of plants, for surgical closings, as well as for adhering two electrically conductive substrates through which an electrical current will be passed. However, preparations which require proteins as starting materials are usually more difficult and costly to prepare and handle than those which employ purely synthetic polymers.

Nowinski, U.S. Pat. No. 4,752,638 teaches the use of specific binding pair members in polymers for selectively removing the complementary binding pair members from a solution. The specific binding pair members are conjugated to monomer units which are then polymerized. Binding pair members are themselves usually proteins, such as antibodies, antigens, antibody receptors, hormone receptors, drug receptors, and transport proteins, and thus, are more difficult and costly than synthetic polymers.

Removal and Separation of Proteins from Biological Samples

Phenol is often used to extract proteins and other material that may interfere with subsequent analysis or manipulation of the DNA. (Kirby, Progr. Nucl. Acid Res. Mol. Biol. vol. 3, p. 1, 1964.) However, phenol poses several safety and health hazards, and is therefore undesirable for occupational safety. Chloroform is also regularly used in the isolation of DNA and RNA, usually in combination with phenol. (Maniatis, et al., Molecular Cloning. A Laboratory Manual, Cold Spring Harbor Laboratory, Cold Spring Harbor, N.Y., 1982, pp. 458–460.) Chloroform is a carcinogen, and so, it too, should be eliminated from the workplace. McCormack U.S. Pat. No. 4,923,978 teaches the use of a solid-phase material with a large surface area and a high concentration of mildly acidic hydroxyls, such as silica, for the separation of proteins from nucleic acids. Svec, U.S. Pat. Nos. 4,889,632 and 4,923,610, teach the use of a macroporous polymeric membrane which is made from a copolymer of a vinyl monomer (which may be hydroxystyrene among other things) and a divinyl monomer. These are demonstrated as having utility in the separation of proteins.

SUMMARY OF THE INVENTION

It is an object of the invention to provide a method of adhering proteins or protein-containing compositions to a substrate.

It is another object of the invention to provide methods of removing proteins from a composition.

It is yet another object of the invention to provide methods of growing cells or tissues in culture on a solid substrate.

It is still another object of the invention to provide methods of purifying viruses, cells or organisms from a biological sample.

It is another object of the invention to provide methods of determining the concentration or presence of a molecule, virus, cell or organism in a sample.

It is still another embodiment of the invention to provide methods of performing a chromatographic separation of proteins.

It is yet another embodiment of the invention to provide a composition for binding molecules, viruses, cells, or organisms.

These and other objects of the invention are provided by one or more of the embodiments described below. In one embodiment of the invention a method of adhering proteins or protein-containing compositions to a substrate is provided which comprises: applying an adhesive formulation to a substrate to form a protein-receptive substrate, said adhesive formulation comprising a nonproteinaceous polymer of monomeric units comprising an aromatic moiety substituted with at least one hydroxyl group and contacting a biologically active composition comprising protein with said protein-receptive substrate.

In another embodiment of the invention a method for removing proteins from a composition is provided wherein the composition is contacted with a substrate to which proteins bind. An adhesive formulation has been applied to enhance the substrate's protein-binding capacity. The adhesive formulation comprises a nonproteinaceous polymer of monomeric units comprising an aromatic moiety substituted with at least one hydroxyl group. In an alternative embodiment of the invention beads are employed as the substrate. The beads comprise a nonproteinaceous polymer of monomeric units which contain an aromatic moiety which is substituted with at least one hydroxyl group.

In another embodiment of the invention a method for growing cells or tissues in culture on a solid substrate is provided. An adhesive formulation has been applied to the substrate which causes the cells or tissues to adhere to it. The adhesive formulation comprises a nonproteinaceous polymer of monomeric units comprising an aromatic moiety substituted with at least one hydroxyl group. In an alternative embodiment beads are employed as a solid substrate. The beads comprise a nonproteinaceous polymer of monomeric units comprising an aromatic moiety substituted with at least one hydroxyl group.

In another embodiment of the invention a method of purifying a virus, cell or organism on a solid support from a biological sample is provided. A protein specific for the virus, cell or organism is contacted with the biological sample. The protein is affixed to the solid support via an adhesive formulation. The adhesive formulation comprises a nonproteinaceous polymer of monomeric units comprising an aromatic moiety substituted with at least one hydroxyl group. In an alternative embodiment of the invention beads are used as the solid support. The beads comprise a nonproteinaceous polymer of monomeric units comprising an aromatic moiety substituted with at least one hydroxyl group. The protein which is specific for the virus, cell or organism is affixed to the beads.

In yet another embodiment of the invention a method is provided for determining the concentration or presence of a molecule, virus, cell or organism in a sample in which a first reactant comprising a protein is affixed to a substrate and a second reactant is contacted with the first reactant to bind said first and second reactants to each other. The first reactant is affixed to the substrate by means of an adhesive formulation. The adhesive formulation comprises a nonproteinaceous polymer of monomeric units comprising an aromatic moiety substituted with at least one hydroxyl group. In an alternative embodiment of the invention beads are used as the substrate. The beads comprise a nonproteinaceous polymer of monomeric units comprising an aromatic moiety substituted with at least one hydroxyl group.

In still another embodiment of the invention a method of performing a chromatographic separation of proteins is provided in which a composition comprising a plurality of proteins is contacted with a chromatographic medium and proteins are separated on the basis of their differential binding capacities to the chromatographic medium. A chromatographic medium is employed to which has been applied: (1) an adhesive formulation, said adhesive formulation comprising a nonproteinaceous polymer of monomeric units comprising an aromatic moiety substituted with at least one hydroxyl group and (2) a protein. In an alternative embodiment beads are employed as the chromatographic medium. The beads comprise a nonproteinaceous polymer of monomeric units comprising an aromatic moiety substituted with at least one hydroxyl group. The beads have protein affixed thereto.

In another embodiment of the invention a composition for binding molecules, viruses, cells, or organisms is provided. The composition comprises a substrate coated with an adhesive formulation comprising a nonproteinaceous polymer of monomeric units comprising an aromatic moiety substituted with at least one hydroxyl group, and a biologically active protein affixed to the adhesive formulation. In an alternative embodiment the composition comprises beads which are made of a nonproteinaceous polymer of monomeric units comprising an aromatic moiety substituted with at least one hydroxyl group. The beads are coated with a protein.

These and other embodiments, which will be described in more detail below, provide the art with rapid and inexpensive means of adhering or binding proteins or protein containing composites to themselves and to other substances. It also provides apparatus for more efficient diagnostic and preparative procedures.

DETAILED DESCRIPTION OF THE INVENTION

It is a finding of the present invention that nonproteinaceous polymers, in a solid or semi-solid state, specifically bind to proteins. Such polymers bear a favorable proportion of aromatic monomeric units which are substituted on the aromatic moiety with at least one hydroxyl group. The discovery of such a solid or semi-solid for protein binding has application with regard to assays to determine the concentration or presence of molecules, viruses, cells or living organisms, protein removal, chromatography on immobilized protein-bearing beads, cell culture, tissue culture, fabrication and implantation of artificial tissues, vessels, implants or grafts, sealing or repairing of disrupted tissues, the operation of medical or veterinary devices, and the operation of electronic devices for the detection of molecules, compounds, viruses, cells or organisms. The protein binding capacity of these polymers can also be used to regulate or temporally extend the release of proteins and protein-containing composites, for example in the human body.

Aromatic monomeric units according to the present invention are chemical structures which have a resonance stabilized, conjugated ring system. These include hydrocarbons, organic or inorganic heterocycles, and elementally pure inorganic compounds. The resonance stabilized, conjugated ring structure is preferably planar. As mentioned above, the ring structure carries at least one hydroxyl group. Other substitutions on the ring system or on the polymer backbone may be used. Some may modulate the affinity of the polymer for proteins. Some may also permit the cross-linking of the polymer. Others may be used to irreversibly chemically bond to proteins.

The polymer may also be a random copolymer, a block copolymer, or a graft copolymer. The aromatic moiety is preferably a phenyl group. Suitable aromatic monomeric units for polymer formation include hydroxyphenyl ethyl-containing groups, especially para-hydroxyphenyl ethyl groups. The ring or polymer backbone may contain other substituents. The polymer is nonproteinaceous, i.e., it is not a naturally occurring, semi-synthetic, or synthetic protein. The backbone of the polymer is not made up of peptide bonds. Typically the aromatic monomeric units will not be amino acids.

Various substituents, proportions of aromatic monomeric units, and resonance-stabilized, conjugated ring systems can be readily tested for use in the present invention by contacting formulations containing them with a surface, removing excess formulation, if necessary, contacting the treated surface with a solution, suspension, powder or aerosol of protein, removing excess protein, if necessary, and measuring the amount of protein bound to the surface or removed from the solution, suspension, etc. Such measurement may be by dye binding, spectroscopy, scintillation counting in the case of radiolabeled protein, enzymatic activity, antibody binding, or direct measurement of the capacity of the treated surface to perform in the desired application.

The polymer of the present invention can be formulated as an adhesive or can be used as a solid, such as in the form of beads. An adhesive formulation according to the present invention contains as its active ingredient the aromatic hydroxylated polymer described above. It may also have one or more diluents, thickening agents, dispersing agents, dyes, or surface conditioning agents. Typically the adhesive formulation will be prepared in an aqueous solution or in a polar organic solvent. Suitable solvents include ethanol, ethyleneglycol diacetate, ethyl acetate, acetone and dimethylsulfoxide. Beads may be impregnated with fluorescent or absorptive dyes, or magnetic or paramagnetic particles.

Proteins or protein-containing compositions according to the present invention include purified and crude preparations of protein, such as cell lysates, as well as viruses, cells, and tissues. Typically the proteins will be biologically active and will retain biological activity when bound to the adhesive formulations and beads of the present invention. Biological activity includes enzyme activity, antibody binding, ability to be recognized and bound by an antibody or receptor, and viability. The proteins may be antibodies, antigens, hormones, receptor molecules, etc. Protein-containing compositions may be viruses, cells, tissues, and organisms.

Substrates which may be coated with the adhesive formulation of the present invention include plastics, natural or synthetic fabrics, membranes or papers, metal, glass, ceramic, semiconductors, cells, tissues, and other protein-containing composites. Suitable plastics include substituted polyethylene, polyamide, polyester, polyether, polysulfone, phenolic resin, epoxy resin, and substituted cellulose. These can be coated or partially coated by any means known in the art, including spraying, dipping, brushing, stamping, extruding, or perfusing.

The coated substrates of the present invention may take many forms. These include beads, strips, wells in multi-well plates, strips or individual units, tubing, mesh, open-cell foam, membranes, papers, needles, surgical threads, surgical staples, microscope slides, surgical instruments, such as knives and scalpels, cell culture vessels, such as flasks and culture dishes.

According to the method of the present invention, after the adhesive formulation is applied to the substrate, a protein-containing composition is contacted with the substrate. The protein may simply be adhered by non-covalent forces, or alternatively the protein may be cross-linked to the adhesive formulation by covalent interactions. This may be desirable for applications such as chromatography, or preparative removal of proteins from biological samples, where further processing is necessary or where the substrate will be recycled.

There are many specific uses to which the adhesive-coated substrates and polymeric beads of the present invention can be put. They can be used to remove proteins from a sample, such as a cell lysate in order to deproteinize the sample. They can be used for growing cells or tissues in culture, by enhancing the adherence of the cells or tissues to the solid substrate. They can be used to purify viruses, cells or organisms from a biological sample, for example by first contacting the adhesive-coated substrate or polymeric beads with a protein which has specific binding capacity for the virus, cell or organism. They can also be used in an assay for determining the concentration or presence of a molecule, virus, cell or organism in a sample by binding a reactant comprising a protein specific for the molecule, virus, cell or organism, to the substrate or beads. They can also be used for chromatographic separation of proteins, for example by binding an antibody or antigen to the substrate or beads. The antibody or antigen is specific for the protein whose separation is desired.

Other uses to which the adhesive-coated substrates and polymeric beads of the present invention can be put include the creation of biocompatible surfaces, the fabrication of protein-bearing composites, including tissue composites, surfaces to support the growth of cells and tissues in vivo, and artificial or repaired tissues, vessels, implants or grafts. In addition, electronically conductive adhesive formulations can be used for attachment of proteins to solid state sensors for the purpose of real-time electronic measurements mediated by proteins or protein-bearing composites, including cells. In such a formulation, dopants have typically been added to render the formulation electrically conductive. The dopants are frequently metals, such as gallium arsenide and silver chloride.

EXAMPLES

Example 1

This example demonstrates the enhanced binding of immunoglobulin-enzyme conjugate to a substrate after application of poly(p-hydroxy-styrene).

96 well poly(vinyl chloride) and poly(styrene) microtiter plates were coated with poly(p-hydroxystyrene) (PHS; MW 6100; pk=10.05 to 10.07) by filling the wells with a 20 mg/ml solution of PHS in ethanol. Control plates were treated with ethanol alone. The solution was immediately decanted, excess PHS solution removed and the plate was incubated at 60° C. for 5 min. to dry the coating. An IgG-peroxidase conjugate of goat anti-rabbit IgG, diluted from 1:1,000 to 1:128,000 in phosphate buffered saline, pH 7.4 (PBS), was added to the wells, 100 ul/well. After incubation for varying times (15, 30, 45, 60 minutes), the wells were rinsed with PBS and assayed for peroxidase activity using 2,2' azino-bis (3-ethylbenzthiazoline-6-sulfonic acid) (ABTS™). The absorbency was then quantitated on an ELISA plate reader. The wells from the PHS-coated plates titered out 4 times as much peroxidase activity as the poly(vinyl chloride) plate and more than 8 times as much activity as the poly(styrene) plate. More activity was bound to the PHS-coated wells at all times examined, and the relative difference between the coated and uncoated wells was similar at all time points tested. No significant differences were noted between PHS coated poly(vinyl chloride) plates and poly(styrene) plates.

Example 2

This example demonstrates the enhancement of binding of protein provided by a copolymer of PHS and styrene.

96 well poly(vinyl chloride) plates were coated with a 70% copolymer of PHS and styrene (MW-30,000) as described in Example 1. An IgG-peroxidase conjugate of goat anti-rabbit IgG, was added to the PHS-coated wells and uncoated wells as described in Example 1. After incubation for 30 minutes, the wells were rinsed with water and assayed for peroxidase activity using ABTS. The peroxidase activity obtained from wells coated with copolymer was 80% of that obtained with PHS alone.

Example 3

This example demonstrates the enhanced binding of cells to slides provided by PHS.

Strips of clear oriented polystyrene were coated with 20 mg/ml PHS (6100 MW) in ethanol and dried at 60° C. Control strips were treated with ethanol alone. Mouse P3XNS1AG4 myeloma cells growing in suspension culture were washed with phosphate buffered saline pH 7.4 (PBS) and added to a dish containing PBS overlaying PHS-coated and uncoated slides. After 30 minutes incubation from a room temperature, the slides were removed and rinsed with PBS and covered with a cover slip. Microscopic examination showed 33.9 cells/field adhered to the surface of the PHS-coated slide whereas the uncoated slide contained 12.2 cells/field, each field being 1 $mm^2$.

Example 4

This example demonstrates the enhanced binding by PHS-coated beads of protein.

¼ inch beads of polystyrene, nylon, polycarbonate, acetate and Delrin™ were coated with 20 mg/ml PHS (6100 or 98700 MW) in ethanol and dried at room temperature. Control beads were treated with ethanol alone. The beads were placed in 96 well polystyrene plates with sells large enough to accommodate the beads, and incubated for 30 min. at room temperature with 200 ul of an IgG-peroxidase conjugate of goat anti-rabbit IgG, diluted 1:10,000 in PBS. The beads were rinsed with water and assayed for peroxidase activity with ABTS. The beads coated with PHS had 2–10 times the amount of peroxidase activity bound as did the uncoated beads.

Example 5

This example demonstrates the internal coating of tubing with PHS and its enhancement of protein binding.

Capillary polyethylene tubing (i.e. z 1 mm) was coated internally with PHS by drawing 40 mg/ml or 20 mg/ml PHS (6100 MW) in ethanol through the tubing and air drying using a suction pump to draw air through the tubing. The tubing was attached to 200 ul capacity pipet tips on a twelve channel pipettor. An amount of diluted (1:10,000) IgG-peroxidase conjugate of goat anti-rabbit IgG which was just sufficient to fill the tubing (25 ul) was drawn into the tubing, allowed to incubate for 5 min. at room temperature, expelled and replenished with fresh solution a total of 5 times. The tubing was rinsed in the same manner with water and then filled with ABTS assay solution, incubated 2 minutes at room temperature and expelled into a microtiter plate for quantitation on a plate reader. The assay step was performed 4 times to give a final assay volume for colored product of 100 ul. Both concentrations for PHS coated tubing gave a saturating response whereas protein adherence to the walls of polyethylene tubing not coated with PHS was undetectable.

Example 6

This example demonstrates the use of cross-linked PHS particles to extract protein from biological samples.

PHS cross-linked with 0.5% divinylbenzene (average diameter=60 microns) was used to extract bovine serum albumin or bovine IgG from aqueous solutions including solutions containing nucleic acids. The PHS suspension (5% in PBS) was mixed in equal volumes with 20 ul of a 1 mg/ml solution of BSA or IgG in PBS, vortexed briefly, centrifuged for 1 min. in a microcentrifuge at full speed to pellet the PHS and ½ the supernatant tested for the presence of protein in a Bradford assay. The amount of protein extracted by 1 mg of cross-linked PHS was 2.5 mg for BSA and 16 mg for IgG.

Example 7

This example demonstrates the binding of an enzyme to a semiconductor chip.

A semiconductor chip was coated with PHS (6100 MW) at 20 mg/ml in ethanol and air dried. A section of the coated chip was then contacted with 0.3 ul of an aqueous solution containing 1 U/ml of alkaline phosphatase at room temperature for 30 minutes. The chip was then rinsed and the enzyme activity assayed using bis-chloroindolphenol nitro blue tetrazolium (BCIP/NBT) substrate. Regions of the chip not exposed to enzyme had little detectable enzyme activity (indicated by the appearance of insoluble blue precipitate on the surface of the chip) whereas exposed regions had detectable activity.

Example 8

This example demonstrates the use of PHS to adhere two mixed-fiber fabrics.

Two strips of cotton/polyester fabric were glued together by applying PHS (30000 MW) at 1 gm/ml in ethanol to an approximately 1 $cm^2$ area, pressing the pieces together and allowing them to dry overnight. The glued fabric was then subjected to a shear test. The bond strength was 160 g/$cm^2$.

Example 9

This example demonstrates the use of PHS to adhere enzyme-antibody conjugates to needles.

21 gauge needles were coated internally with PHS by drawing 20 mg/ml PHS (6100 MW) in ethanol through the needles and drying the coated needles with a stream of nitrogen. The needles were attached directly to an eight channel pipettor. An amount of diluted (1:10,000) IgG-alkaline phosphatase conjugate of goat anti-rabbit IgG which was just sufficient to fill the needles (25 ul) was drawn into the tubing, allowed to incubate for 5 min. at room temperature, expelled and replenished with fresh solution a total of 5 times. The tubing was rinsed in the same manner with water and then filled with p-nitrophenylphosphate (pNPP) assay solution, incubated 2 minutes at room temperature and expelled into a microtiter plate for quantitation on a plate reader. The assay step was performed 4 times to give a final assay volume for colored product of 100 ul. Needles coated with PHS gave a saturating response whereas needles not coated with PHS gave an undetectable response.

Example 10

This example demonstrates the enhancement of protein binding to multi-well plates used for an enzyme linked immunoadsorbant assay.

In an ELISA assay, BSA was coated onto 96 well polystyrene plates at room temperature for 30 minutes in a 100 ul volume in PBS pH 7.4, at concentrations of 1 ug to 0.5 pg/well. The plates were rinsed and 100 ul of rabbit anti-BSA antibody was added to the wells in dilutions of 1:1,000 to 1:128,000 in PBS. After 30 minutes incubation at room temperature, the rabbit antibody was removed and goat-anti rabbit IgG-peroxidase conjugate was added at a dilution of 1:1,000 in PBS. After the last step, the conjugate was removed by washing and ABTS substrate was added. Plates coated with PHS gave an equivalent response at concentrations which were 16–32 times lower than those on uncoated plates.

Example 11

This example demonstrates the adhesion of protein to metal mediated by PHS.

PHS (6100 MW) was dissolved at 20 mg/ml in either ethanol, ethyleneglycol diacetate, ethyl acetate, acetone or dimethylsulfoxide. Each PHS solution was applied in a single drop to the surface of an anodized aluminum plate and dried at 60° C. The plate was then immersed in PBS containing alkaline phosphatase at a concentration of 0.01 U/ml. After 30 min. incubation at room temperature, the plate was rinsed with PBS to remove unbound enzyme and immersed in BCIP/NET substrate to detect the presence of the enzyme. Each of the PHS coated regions developed color indicating the presence of alkaline phosphatase. Uncoated regions did not develop detectable color. No significant differences in the extend of color development were observed among the areas coated with different PHS solutions.

Example 12

This example demonstrates the binding of protein to a chromatographic column packed with PHS-coated beads.

A macroreticular resin (XAD-8; 160 m2/gm, pore size=225 angstoms) was coated with PHS (98,700 MW) dissolved in ethanol at 10 mg/ml and dried at 60° C. under vacuum. Control beads were treated with ethanol alone and dried. After rehydration, a solution containing 2.5 ug BSA was passed through a 0.5 ml resin bed. No significant amounts of protein could be detected in the eluate of the PHS-treated column indicating complete adsorption of the protein. On the other hand, no detectable amounts of protein were bound to the control column.

Example 13

This example demonstrates the binding of enzymes to PHS-coated nylon membranes.

Nylon membranes (MAGNA nylon; MSI) were cut into strips 3 cm×12 cm. Half of each strip was coated with PHS (6100 MW) in ethanol at 20 mg/ml and dried at 60° C. The strips were then briefly immersed in 0.1 N NaOH, rinsed in PBS and placed into a 2 ul×13 well slot-blot apparatus. 100 ul samples of either alkaline phosphatase or goat anti-rabbit IgG-peroxidase conjugate were added to the slots and drawn through the membrane. The amount of protein added to the first slot was 1 U for alkaline phosphatase and a 1:1000 dilution of conjugate with an ELISA titer of 1:60000 for the goat anti-rabbit IgG-peroxidase. Each subsequent slot received a 1:1 dilution of protein over a total of 11 slots to give a final dilution factor of 1:1000 relative to the starting amount. The blots were then rinsed with 10 mM Tris-HCl, 1 mM EDTA buffer pH 8, removed from the apparatus and immersed in buffer containing BCIP/NET substrate for alkaline phosphatase or 4-chloronapthol substrate for peroxidase. The amount of detectable enzyme activity was 4–10 fold greater on the hydroxystyrene coated side of each membrane. When the concentration of BCIP/NET substrate was reduced by a factor of 10, the differences were even more striking with no detectable loss of activity for alkaline phosphatase bound to hydroxystyrene coated nylon and almost complete loss of activity on uncoated nylon.

Example 14

This example demonstrates the use of halogenated PHS for coating multi-well plates.

96 well poly(vinyl chloride) plates were coated with brominated PHS and tested for protein binding as described in Example 1 for PHS using a 30 minute incubation time. The amount of protein bound to the wells of plates coated with brominated PHS was 30–35% less than that bound to the wells of plates coated with unsubstituted PHS, but more than 4 times greater than that bound to the wells of uncoated plates.

Example 15

This example demonstrates the use of PHS to bind an enzyme to ceramic.

A ceramic plate was coated with PHS (6100 MW) in ethanol at 20 mg/ml and air dried. 20 ul aliquots of PBS containing 1 U alkaline phosphatase were dropped onto PHS-coated and uncoated regions of the ceramic material and incubated for 30 minutes in a humid environment to prevent evaporation of the solution. The enzyme was rinsed off the plate and BCIP/NET substrate added. The amount of alkaline phosphatase detected on PHS-coated areas of the ceramic plate was substantially greater than that seen on uncoated areas.

What is claimed is:

1. A method of adhering protein-containing compositions to a substrate, comprising:

applying an adhesive formulation to a substrate to form a protein-receptive substrate, said adhesive formulation comprising a nonproteinaceous polymer of monomeric units comprising an aromatic moiety substituted with at least one hydroxyl group;

contacting a biologically active composition comprising protein with said protein-receptive substrate to adhere protein in said biologically active composition to said protein-receptive substrate, wherein adherence of said protein to said substrate is enhanced by said adhesive formulation.

2. The method of claim 1 wherein said aromatic moiety is a phenyl group.

3. The method of claim 1 wherein said hydroxyl group is a para-hydroxyl relative to said aromatic moiety's attachment site to said polymer's backbone.

4. The method of claim 1 wherein the adhesive formulation comprises an aqueous solution.

5. The method of claim 1 wherein the adhesive formulation comprises a polar organic solvent.

6. The method of claim 1 wherein the substrate is nonproteinaceous.

7. The method of claim 1 wherein the substrate comprises a plastic.

8. The method of claim 7 wherein the plastic is selected from the group consisting of polyamide, polyester, polyether, polysulfone, phenolic resin, epoxy resin, substituted polyethylene, and substituted cellulose.

9. The method of claim 1 wherein the substrate is a membrane.

10. The method of claim 8 wherein the substrate is a membrane.

11. The method of claim 1 wherein the substrate is metal.

12. The method of claim 1 wherein the substrate is glass.

13. The method of claim 1 wherein the substrate is ceramic.

14. The method of claim 1 wherein the substrate is a semiconductor.

15. The method of claim 1 wherein the substrate is a natural fabric.

16. The method of claim 1 wherein the substrate is a synthetic fabric.

17. The method of claim 1 wherein the substrate comprises a biological tissue.

18. The method of claim 1 wherein the substrate comprises cells.

19. The method of claim 1 wherein said composition comprising a protein comprises cells.

20. The method of claim 1 wherein said composition comprising a protein comprises a biological tissue.

21. The method of claim 1 wherein said composition comprising a protein consists essentially of a cell lysate.

22. The method of claim 1 wherein said composition comprising a protein consists essentially of a purified protein.

23. The method of claim 1 wherein said composition comprising a protein consists essentially of an enzyme.

24. The method of claim 23 further comprising the step of: cross-linking said enzyme to said polymer.

25. The method of claim 1 further comprising the step of:

contacting said biologically active composition comprising protein which has been adhered to said protein-receptive substrate, with a species selected from the group consisting of a virus, and a cell, to bind said species to said biologically active composition.

26. The method of claim 1 wherein said biologically active composition consists essentially of protein.

27. The method of claim 1 further comprising:

contacting an organism with said protein which has been adhered to said substrate, to bind said organism to said protein.

* * * * *